United States Patent
Collins et al.

(10) Patent No.: US 9,738,598 B2
(45) Date of Patent: *Aug. 22, 2017

(54) MODULARIZED SYSTEM AND METHOD FOR UREA PRODUCTION USING A BIO-MASS FEEDSTOCK

(71) Applicant: 4A Technologies, LLC, Doral, FL (US)

(72) Inventors: Terry R. Collins, Stillwater, OK (US); James L. Simonton, Lubbock, TX (US); Mario G. Beruvides, Lubbock, TX (US); Jessie Lozada, Jr., Shallowater, TX (US)

(73) Assignee: Trimec Biogas Technology Ltd. (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/167,199

(22) Filed: May 27, 2016

(65) Prior Publication Data

US 2016/0326100 A1 Nov. 10, 2016

Related U.S. Application Data

(63) Continuation of application No. 14/143,890, filed on Dec. 30, 2013, now Pat. No. 9,352,329, which is a continuation-in-part of application No. 13/058,308, filed as application No. PCT/US2009/053547 on Aug. 12, 2009, now Pat. No. 8,618,325.

(60) Provisional application No. 61/088,253, filed on Aug. 12, 2008, provisional application No. 61/088,178, filed on Aug. 12, 2008.

(51) Int. Cl.
| | |
|---|---|
| *C07C 273/04* | (2006.01) |
| *C07C 273/10* | (2006.01) |
| *B02C 19/00* | (2006.01) |
| *C10L 5/44* | (2006.01) |
| *B02C 21/00* | (2006.01) |
| *C10L 5/36* | (2006.01) |
| *C10J 3/72* | (2006.01) |
| *C10J 3/82* | (2006.01) |

(52) U.S. Cl.
CPC ........ *C07C 273/10* (2013.01); *B02C 19/0056* (2013.01); *B02C 21/00* (2013.01); *C10J 3/72* (2013.01); *C10J 3/82* (2013.01); *C10L 5/363* (2013.01); *C10L 5/44* (2013.01); *C10J 2300/0906* (2013.01); *C10J 2300/0916* (2013.01); *C10J 2300/1668* (2013.01); *Y02E 50/10* (2013.01); *Y02E 50/30* (2013.01)

(58) Field of Classification Search
CPC .................................................. C07C 273/04
USPC ......................................................... 504/67
See application file for complete search history.

(56) References Cited

U.S. PATENT DOCUMENTS

| | | | |
|---|---|---|---|
| 4,224,299 A | 9/1980 | Barber et al. | |
| 5,681,471 A | 10/1997 | Silverstein | |
| 6,084,129 A * | 7/2000 | Romiti | C07C 273/04 |
| | | | 504/327 |
| 8,618,325 B2 * | 12/2013 | Collins | C07C 273/04 |
| | | | 564/67 |
| 2002/0055545 A1 | 5/2002 | Sheppard et al. | |
| 2007/0000177 A1 | 1/2007 | Hippo et al. | |
| 2008/0097137 A1 | 4/2008 | Chapman et al. | |

FOREIGN PATENT DOCUMENTS

| | | |
|---|---|---|
| DE | 102007004294 | 7/2008 |
| EP | 1669434 | 6/2006 |
| WO | 02090250 | 11/2002 |
| WO | 2007081296 | 7/2007 |
| WO | 2008073186 | 6/2008 |

* cited by examiner

*Primary Examiner* — Sudhakar Katakam
*Assistant Examiner* — Kofi Adzamli
(74) *Attorney, Agent, or Firm* — GableGotwals

(57) ABSTRACT

A modular system and method for producing urea from bio-mass includes means and steps for "homogenizing" a biomass feedstock stream having components with different bulk density BTU content into a stream having a consistent bulk density BTU content. The steps include cleaning the incoming bio-mass feedstock stream to remove non-organic matter, blending the cleaned bio-mass feedstock stream to obtain a homogeneous blend having a consistent bulk density BTU content, and milling the homogeneous blend bio-mass feedstock stream to a predetermined size no greater than 12 mm.

15 Claims, 7 Drawing Sheets

MODULARIZED SYSTEM AND METHOD FOR UREA PRODUCTION USING A BIO-MASS FEEDSTOCK

CROSS-REFERENCE TO RELATED APPLICATIONS

This application is a divisional of U.S. patent application Ser. No. 14/143,890 filed Dec. 30, 2013, now U.S. Pat. No. 9,352,329, which is a continuation-in-part of U.S. patent application Ser. No. 13/058,308 filed on Feb. 9, 2011, now U.S. Pat. No. 8,618,325, which is United States National Phase of PCT Patent Application No. US2009/053547 filed on Aug. 12, 2009, which was published in English on Feb. 18, 2010 under Publication No. WO 2010/019662 A1, which claims priority to U.S. Provisional Patent Application Nos. 61/088,253 and 61/088,178 both filed Aug. 12, 2008, which are incorporated herein by reference.

BACKGROUND OF THE INVENTION

The present invention relates generally to the conversion of bio-mass and bio-mass waste streams via the process of bio-gasification and, more specifically, to the conversion of bio-mass and bio-mass waste streams to produce higher order chemicals such as urea.

Although the conversion of biomass and biomass waste streams via the process of bio-gasification (syngas) to produce usable products has been accomplished to varying degrees of effectiveness and efficiency in the past, the gasification of bio-mass to produce urea is yet untapped. The main technical barriers cited by the U.S. Department of Energy to utilizing bio-mass-based syngas to produce higher order chemicals such as urea are: (1) feed process and handling; (2) gasification/conversion; (3) gas cleanup and catalytic conditioning; (4) syngas utilization; (5) process integration; and (6) process control, sensors, and optimization.

Prior art gasification systems using bio-mass as a feedstock stop at the formation of syngas. Because this syngas is of low quality, it cannot be directly used to produce higher order chemicals such as urea. Rather, the syngas is used to power generators or mixed with a natural gas stream being converted to urea (see technical barrier 3 above). In addition, the prior art requires large production units or large-scale plants. Because of the high volume of production required by these plants, the input material must be run through sequential processing units before the syngas can be converted to ammonia. Because of the size of the plants, the plants tend to be located far away from all of the ready and available sources of bio-mass feedstock, thereby increasing transportation costs or—in the case of remote rural or geographically challenging areas—making it extremely difficult if not economically infeasible to locate a plant or transport the bio-mass to the plant. This bio-mass feedstock, which tends to be stored in fields prior to it being transported to the plant and processed, is usually dirty, of low storage density, and difficult to handle (see technical barrier 1). Furthermore, the bio-mass feedstock varies considerably in its processing characteristics both between and within types of bio-mass. This variation makes it difficult for plants to control, much less optimize, the conversion process and maintain a high level of conversion efficiency (see technical barriers 2 & 4-6 above).

BRIEF SUMMARY OF INVENTION

A modular system and method for producing urea from bio-mass includes the steps of cleaning a bio-mass feedstock to remove substantially all non-organic matter; blending the cleaned bio-mass feedstock to obtain a substantially homogeneous blend; pelletizing the blended bio-mass feedstock to a substantially uniform size; gasifying the pellets in a gasifier; and combining a resultant $CO_2$ stream from the gasifier with $NH_3$ to form urea. The cleaning step cleans the bio-mass feedstock so that it preferably includes no more than 1% non-organic matter by weight. The cleaning step may also include the sub-step of sizing the bio-mass feedstock to a predetermined size of about 0.75 to 1.25 cm (¼ to ½ in.) and reducing the bulk size of the bio-mass feedstock by about 80%.

The bio-mass feedstock, which preferably has a moisture content of less than 15% by weight, may include a single bio-mass material having different processing characteristics or two or more bio-mass materials having a different processing characteristic such as density or calorific burn value. The pelletizing step pelletizes the cleaned bio-mass feedstock and provides pellets having substantially the same processing characteristics. Similarly, pellets produced from one type or quality of bio-mass feedstock may be combined and blended with pellets produced from another type or quality of bio-mass feedstock to produce a blend of the two pellet streams whose processing characteristics can be adjusted to maintain a consistency in temperature and burn quality for improved or optimal gasification.

The gasifying step preferably includes the sub-step of pulverizing the pellets to a fine particle size of about 1 mm. This fine particle size provides for a more efficient burn and a higher conversion rate of the bio-mass to gasified bio-mass (syngas). To further improve the efficiency and conversion performance of the gasifier, the gasifying step may also include the sub-step of injecting an organic oil into the input bio-mass feed stream or mist. The feed rate to the gasifier may be controlled so that the burn temperature of the gasifier, which may be in a range of 600° to 850° C., does not vary by more than ±25° C. By controlling the quality of the incoming bio-mass, pulverizing the bio-mass to a fine particle size, and regulating the feed rate in response to critical process parameters, the gasifier is effective for a conversion efficiency of about 98% or more.

The resultant syngas stream from the gasifier is cleaned and then compressed to a high pressure of about 6,000 to 7,000 psi. This pressure is roughly two times higher than the pressure used in prior art plants. The ammonia stream is processed in a bypass recycling loop system at 30% conversion rate at a high pressure of about 6,000 to 7,000 psi.

The system and method according to this invention allows for small scale, cost effective conversion of bio-mass to higher order chemicals such as urea. For example, the equipment associated with each of the various process steps may be skid mounted or contained within the footprint of a standard 48-foot flatbed trailer. The modules may be interconnected at a single site or the cleaning module, pelletizing module, and gasifying module (and each module's associated processing steps) may each occur at a different geographical location. Modularity also allows the system to travel to the site of a bio-mass source, such as a farming community located in a remote rural area, where the method can be practiced on site.

An object of this invention is to provide a urea production plant that has a smaller footprint than conventional designs, is modular in construction, and can be easily transported, assembled for use, updated, modified, disassembled after use, and re-used. Another object of this invention is to provide a cost effective, low volume production plant. Another object of this invention is to provide a plant that can accommodate a bio-mass feedstock that is typically found in most rural areas—that is, of varying types, sizes, and process characteristics—and yet still achieve a high level of performance in converting this non-homogeneous bio-mass feedstock to a syngas useful in producing other products. Yet another object of this invention is to provide a bio-mass feedstock that is easily handled and provides increased density, reduced storage requirements, increased storage longevity, and reduced fire hazard potential. A further object of this invention is to provide a much cleaner and more uniform bio-mass feedstock to the gasification process than current processes provide. It is yet another object of this invention to provide a bio-mass feedstock that burns more evenly and reduces the production of by-products such as tar. Another object of this invention is to provide a clean syngas to the urea/ammonia conversion units. Still yet another object of this invention is to provide a bypass recycling loop system run at very high pressures to achieve almost a 100% conversion rate. A final object of this invention is to provide a process that simultaneously addresses all six of the technical barriers to the use of bio-mass to produce higher order chemicals such as urea.

DETAILED DESCRIPTION OF THE PREFERRED EMBODIMENTS

Figure 1:
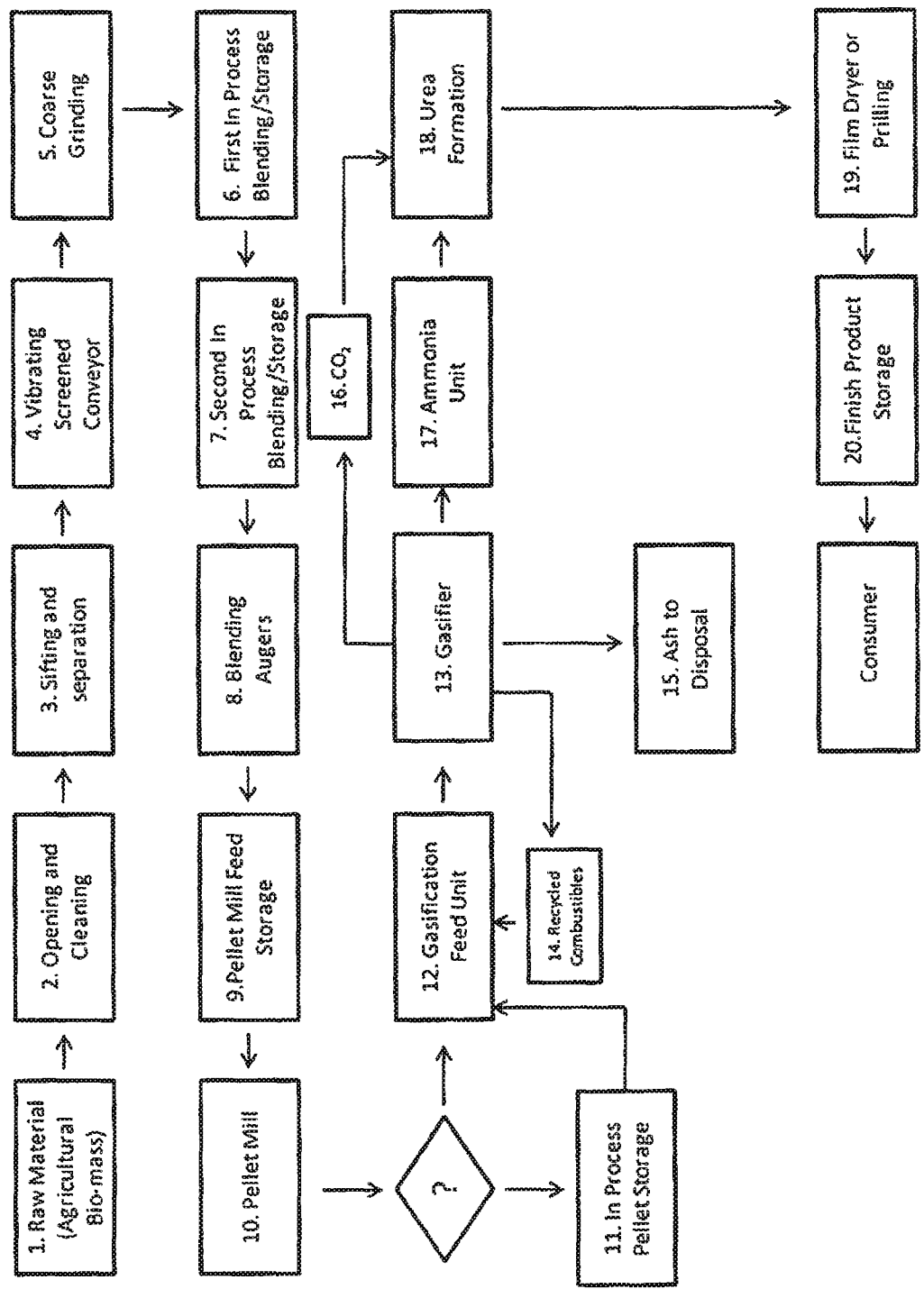
FIG. 1 is a process flow diagram of a urea production process that converts agricultural bio-mass into urea. The agricultural bio-mass is pelletized to a consistent density prior to being fed into a gasification unit.
Figure 2:
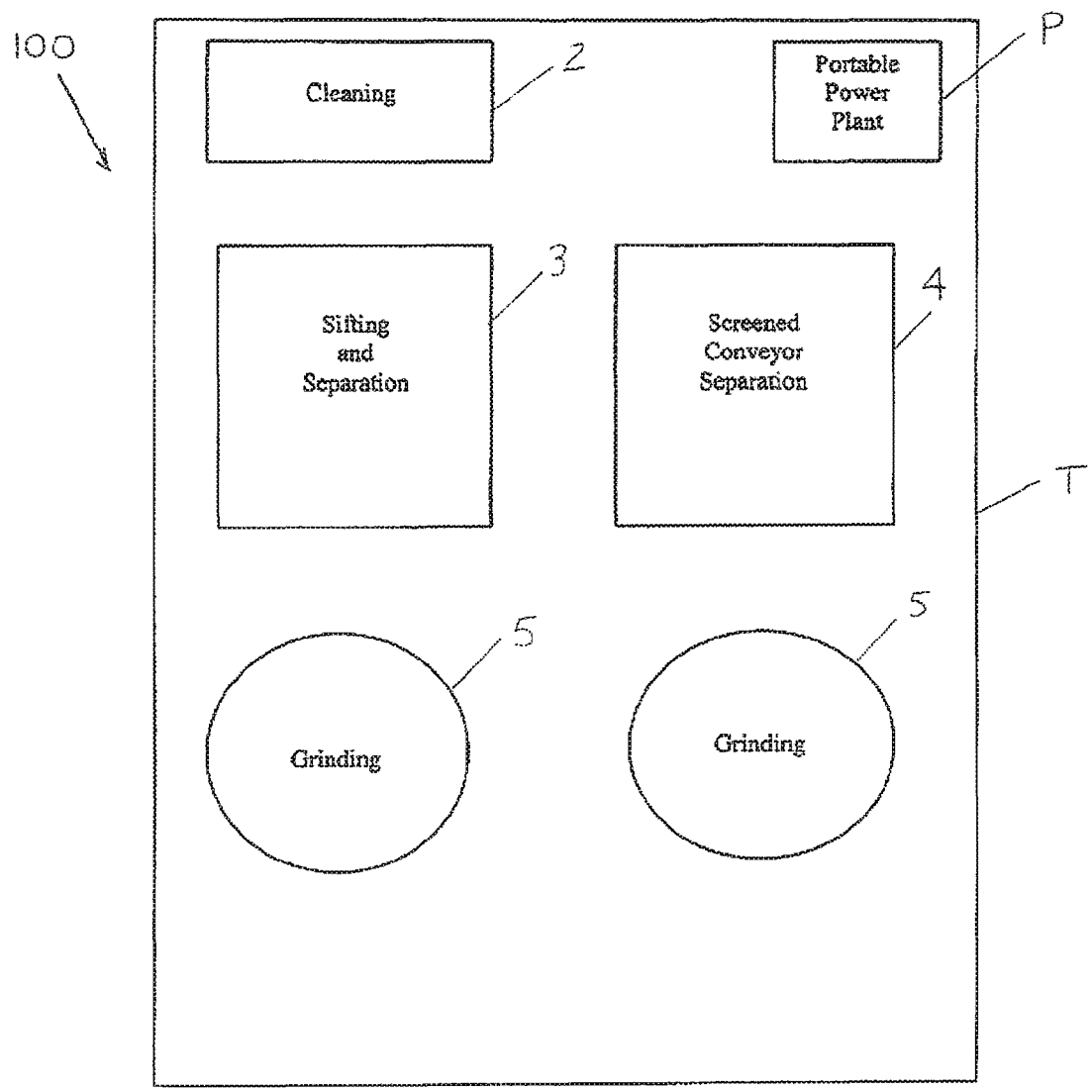
FIG. 2 is a block layout of the feedstock preparation module arranged on a standard 48-foot flatbed trailer.
Figure 3:
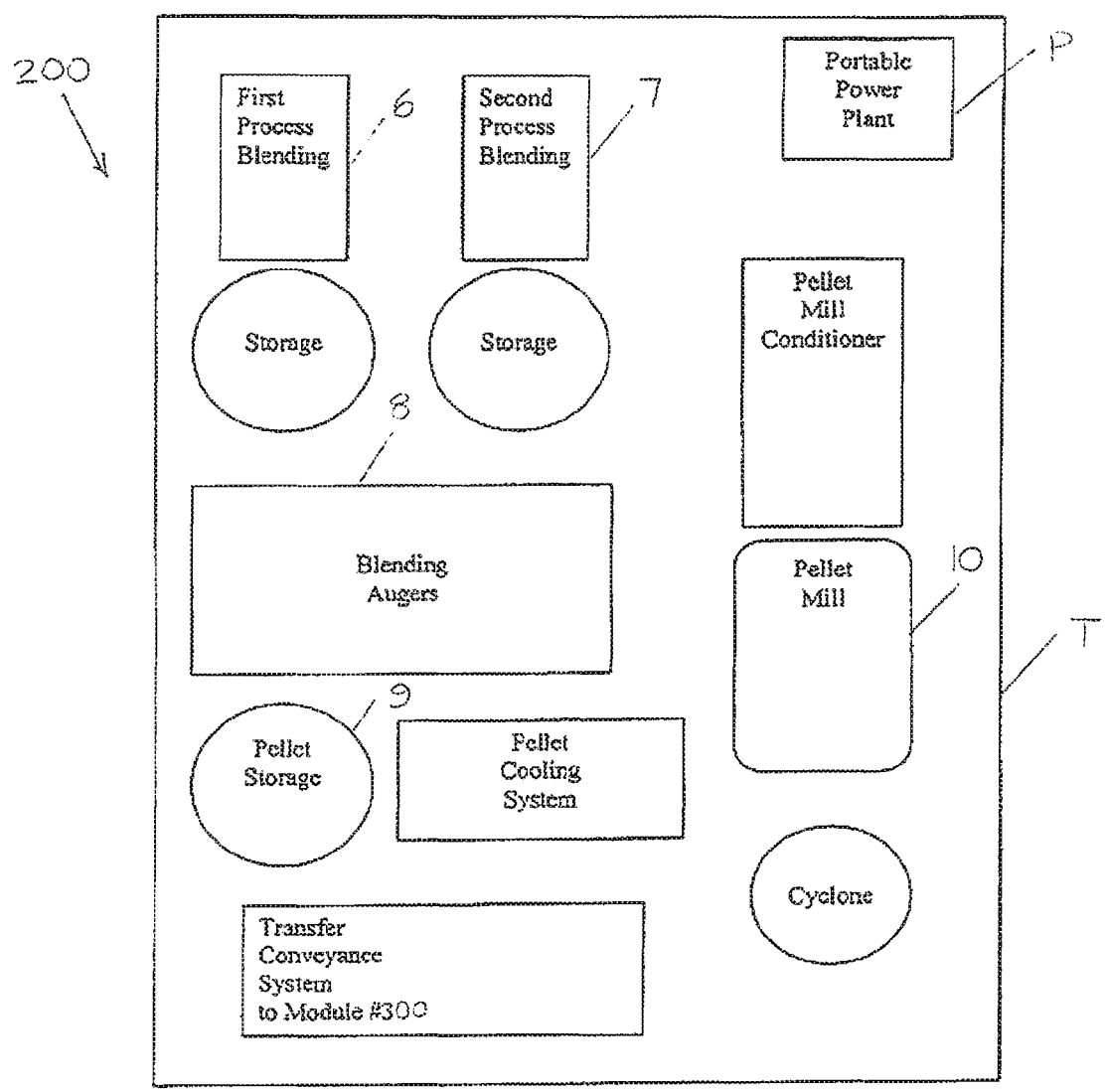
FIG. 3 is block layout of the pelletizing module arranged on a standard 48-foot flatbed trailer. The pelletizing module may be skid mounted.
Figure 4:
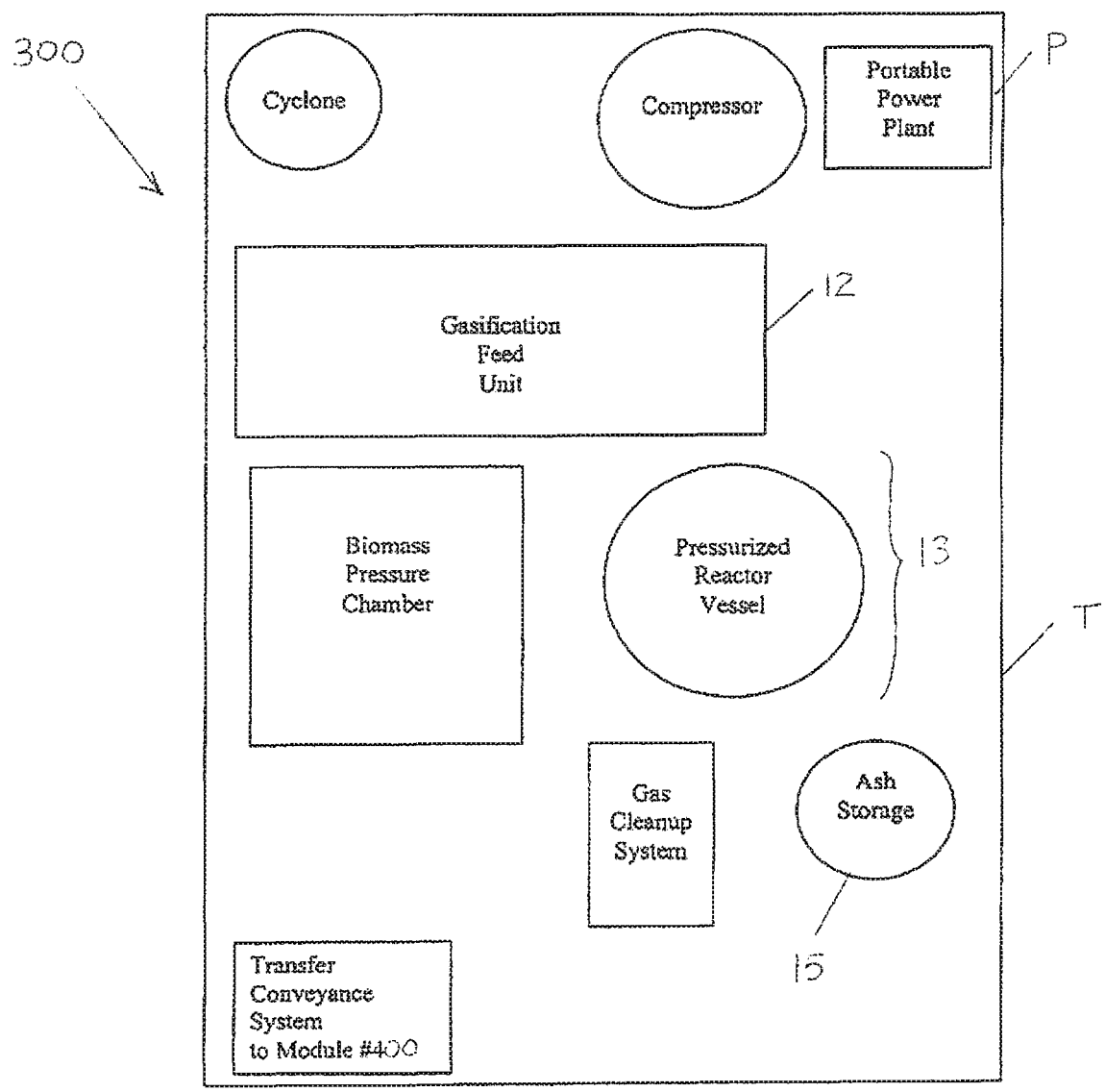
FIG. 4 is a block layout of the gasification system module arranged on a standard 48-foot flatbed trailer.
Figure 5:
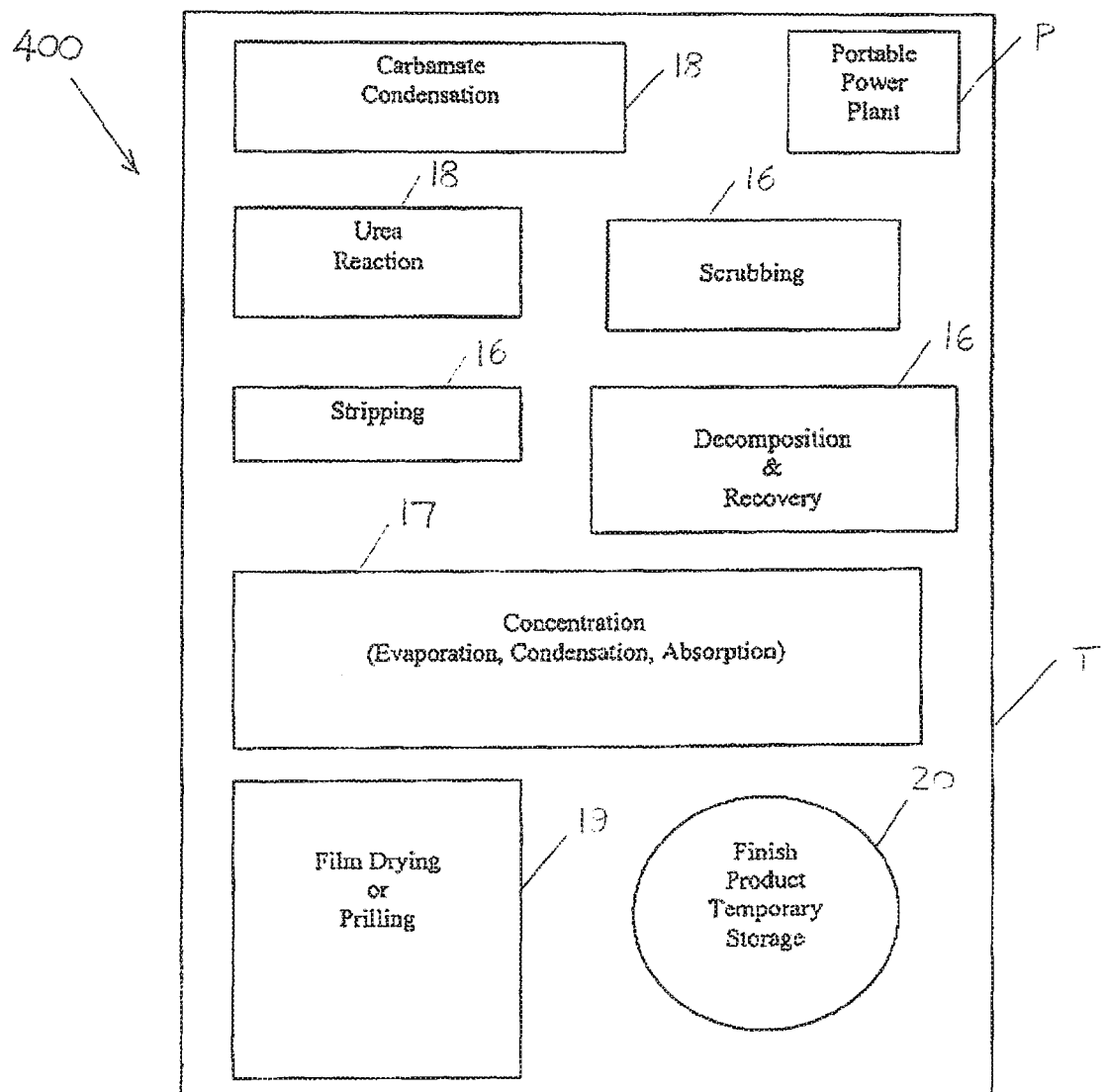
FIG. 5 is a block layout of the urea conversion module arranged on a standard 48-foot flatbed trailer.
Figure 6:
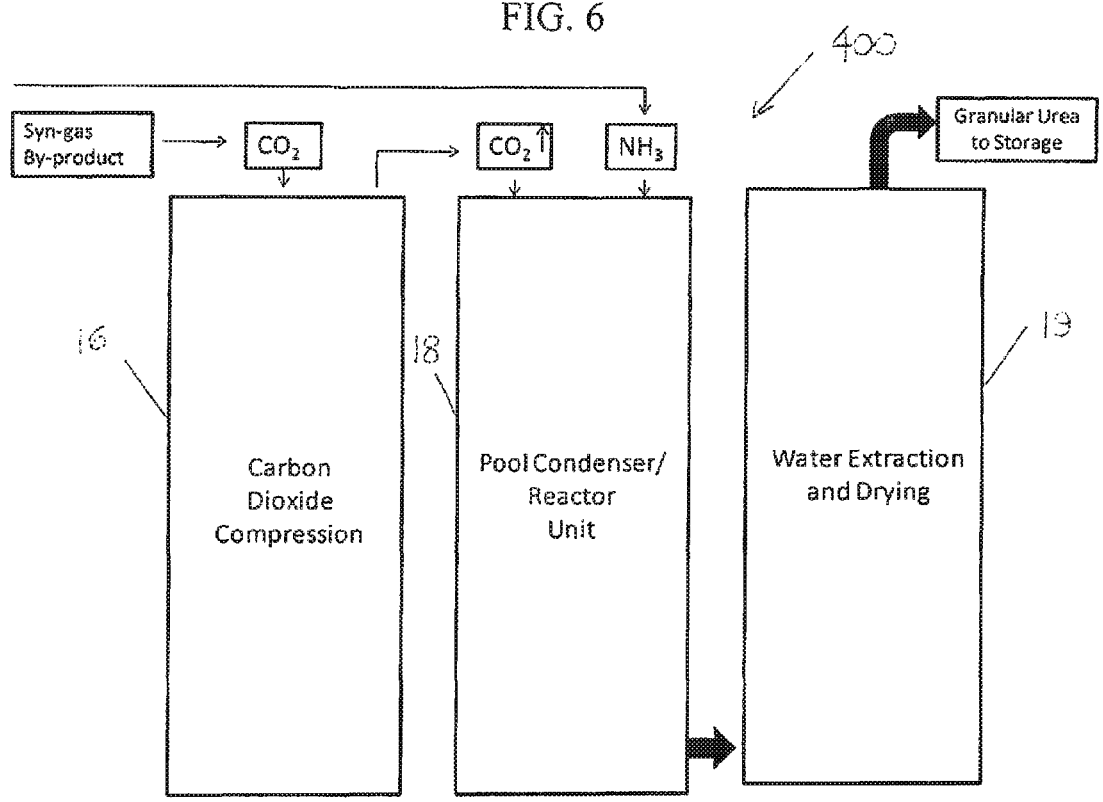
FIG. 6 is a schematic representation of the interrelationship between the carbon dioxide compression component, condenser/reactor, and water extraction and drying components of the urea conversion module and the syngas stream.
Figure 7:
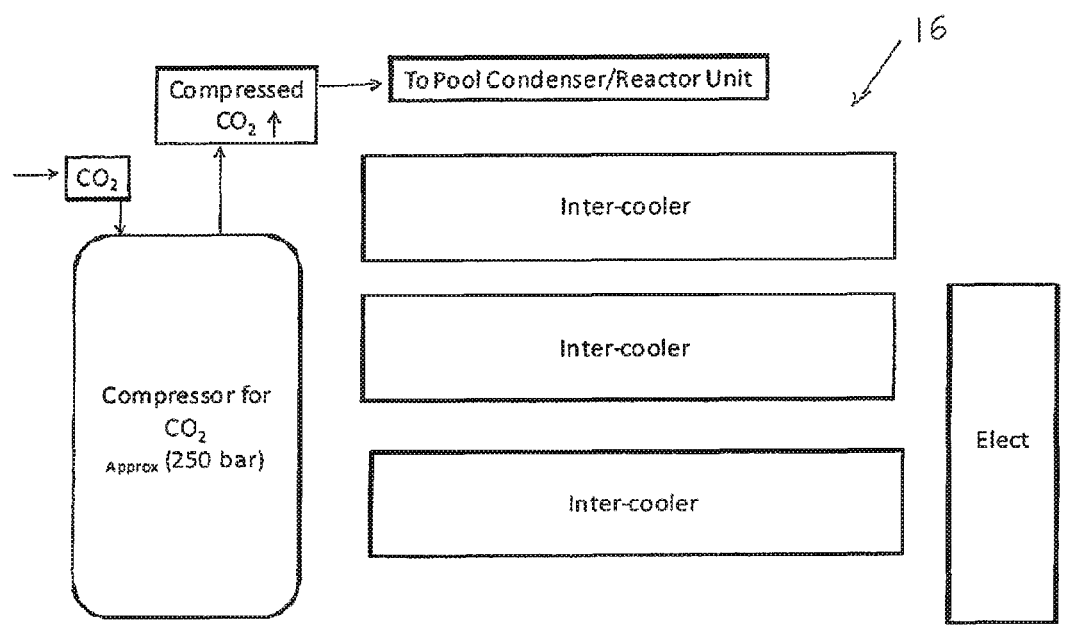
FIG. 7 is a schematic representation of the carbon dioxide compression component of an the urea conversion module.
Figure 8:
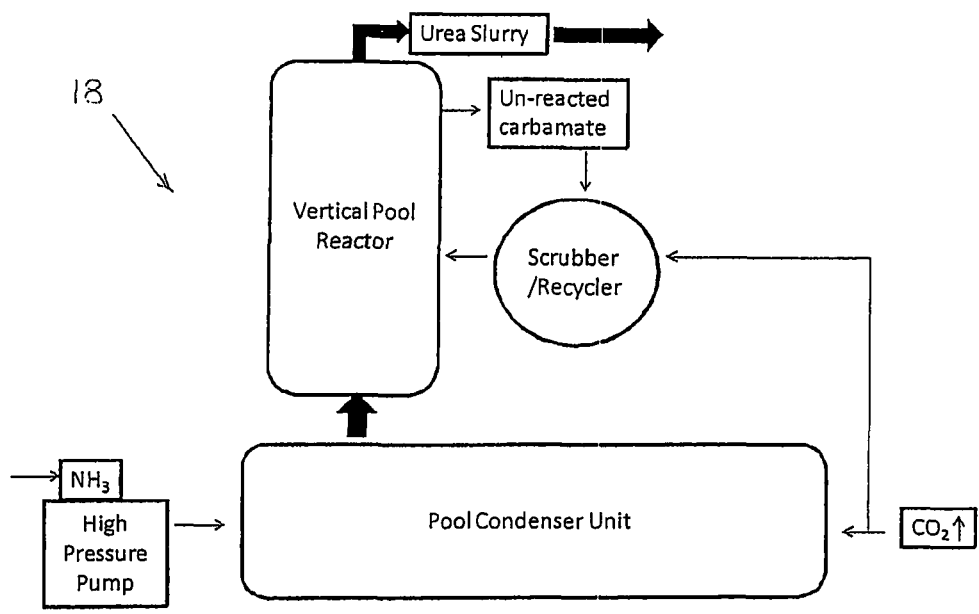
FIG. 8 is a schematic representation of the pool condenser/reactor component of the urea conversion module.
Figure 9:
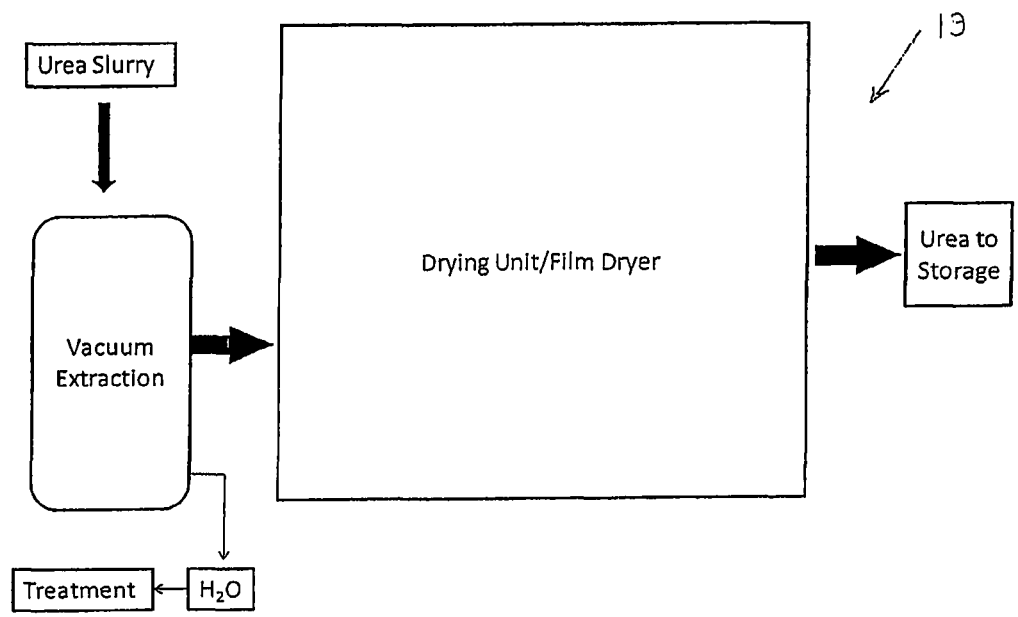
FIG. 9 is a schematic representation of the water extraction and drying component of the urea conversion module.

All six technical barriers listed in the Background of the Invention section are addressed in the following technical description for the conversion of biomass via the process of gasification to produce urea. The process—which is designed for cost effective low volume production (e.g. feed rates of 1 to 5 tons per hour) and modularized for improved process control and portability—provides a clean and consistent bio-mass feedstock to the gasifier. An on-demand organic oil injector is used to supplement the bio-mass mist in the gasification unit to maintain a constant, low fluctuating burn of the bio-mass. The gasification process also has a feed control system that serves as a bio-mass feed regulator. The gasified bio-mass (syngas) is then cleaned by running the syngas through a set of cyclones (gas cleaning system-scrubbers) before introducing the syngas to the ammonia/urea formation units.

Unlike the prior art systems, the process includes a bypass loop recycle system at 30% conversion rate run at very high pressures (about 6,000 to 7,000 psi) which results in almost 100% conversion rates. The higher pressures allow for better separation of the chemical break-down during the creation of the ammonia. This conversion performance cannot be achieved with the same level of productivity by the high volume, low pressure processes in common use in today's industry. These prior art processes run at pressures approximately one-half the pressure of the process described herein.

The gasification of biomass using this process can also be used with modifications to generate other usable products. Addressing in conjunction all six of the technical barriers constitutes one of the unique features of the invention. Unlike the prior art processes, which seek to optimize each and every step of the process, the process according to this invention incorporates the concept of systems "sub-optimization" developed by the American scholar and researcher Dr. W. Edwards Deming. The concept of sub-optimization states that a whole process (system) may result in sub-optimized performance by optimizing each individual sub-process (sub-system). True systems optimization is obtained by sub-optimizing sub-systems performance, when necessary, to achieve the optimization of the whole or complete system. The input of materials to the process described herein goes through extra processing, namely, eight process steps of coarse to fine grinding and mixing with an additional pelletizing step. This extra processing constitutes a sub-optimization of the preparatory process but leads to an overall optimization of the complete process. Requiring additional in-process equipment, capital expenditure and processing time and effort in feedstock preparation optimizes the critical processes of gasification and ammonia/urea production, thereby addressing all six technical barriers.

A urea production plant made according to this process preferably incorporates a modular construction, another unique feature of the invention. The plant is based on a five module configuration that is designed to minimize on-sight erection and start-up time/cost. The total package design improves the overall reliability along with flexibility. Modular construction minimizes the footprint of the production units while maintaining ease of operation and maintenance. Modular construction increases the ease with which updates and modifications can be performed as well as allowing units to be built in a central location and shipped anywhere around the world, or manufactured in the country of operation using standardized plans and specifications. Modular construction also allows for certain modules, such as the feedstock preparation module, to travel to the source of the bio-mass feedstock. In addition, modularization allows for the upgrade of the production plant by replacing specific modules when technical advances in such modules are developed without affecting the other modules that comprise the whole system (plant). This also allows for reduced downtime for process upgrades and maintenance.

I. Process Description

The process for the production of urea via the gasification of bio-mass, hereinafter called the "urea plant," includes 20 distinct process steps as presented in FIG. 1. Each process step is herein described, specifying the instrumentation (apparatus), processing procedure, technical requirements, uniqueness of the design versus prior art, and related art and processes.

Process Step 1—Raw Material (Bio-Mass) Intake

The urea plant has a high degree of bio-mass feedstock flexibility. Once the feedstock weight, density and BTU/calorific values are known, the process parameters (computer numerically controlled) can be adjusted to obtain optimal gasification of the biomass. This addresses technical barriers 5 and 6 listed above. Bio-mass feedstocks that can be used in this process include but are not limited to cotton gin waste, corn stover, rice hulls, sugar cane bagasse, paper goods (newspaper, office usage, cardboard, etc.), wood (wood mills, municipal waste wood, etc.), coffee bean pulp, nutshells, straws, grasses, animal manure, mesquite, other crop residues, African palm (palm oil), and other bio-mass material. Any bio-mass dried to a moisture content of less than 15%, cleaned to remove non organic matter, and ground to a consistent size (via process steps 2 to 5 below) is a potential raw material stock either alone or in combination with other dried bio-mass for the production of urea using this process. For example, the bio-mass that is fed into the process may include a mix of cotton gin waste, field-harvested cotton stalks, corn stover, and straw. The system achieves high levels of efficiency, productivity, and economies as long as there is a highly blended consistent feedstock.

The consistency of the feedstock for the gasification process has been a key stumbling block that has limited the use of biomass in the past. The raw material preparation (steps 2 through 12 in FIG. 1) addresses several key biomass feed issues for gasification—namely, technical barriers 1-3 above—and improves the overall process dependability, production throughput efficiency and productivity.

Process Step 2—Opening and Cleaning

To obtain the efficiencies and productivity of the gasification system, the raw material (biomass) must be furnished as a homogenous blend (particulate size, blend, and BTU value) in order to maintain high operations standards and reduce the build-up of by-products that reduce process efficiencies and increase maintenance costs. This is achieved through a series of operations that remove non-organic material and blend, reduce, and condense the raw bio-mass feedstock. The preparation of the raw material begins with the opening and cleaning process where the biomass that is delivered to the urea plant is dumped into an open end screw conveyor that transports the raw material to the sifting and separation process step.

Process Step 3—Sifting and Separation

In sifting and separation, when the material is being conveyed through the screw conveyor, the conveying is done over a fine mesh bottom to obtain the first level of raw material cleaning by removing small non-organic particulate matter (specifically sand) that builds up on most biomass that is usually stored in fields and exposed to the elements.

Process Step 4—Vibrating Screened Conveyance

The next step in the process is conveying the bio-mass via an elevated vibrating conveyor with a mesh bottom. This next step is also done to remove non-organic particulate matter. The vibrating conveyor is a more active removal system. This conveyor is also required to elevate the bio-mass to be gravity fed to the next processing step, coarse grinding. The conveying of the material while assisting in the removal of non-organics can also be accomplished by such equipment as a screw auger or pneumatic conveyors that have some form of screening for removal of non-desirable materials from the raw material input.

Process Step 5—Coarse Grinding

Coarse grinding is the first step of the raw material preparation in which uniformity of size is achieved, preferably in a range of about 0.75 to 1.25 cm (¼ to ½ in.). Most bio-mass, and in particular bio-mass obtained from agricultural production, is a combination of different bio-mass components (such things as husks, seeds, stalks, leaves, etc). The bio-mass, which arrives in varying sizes and shapes, is coarsely ground in a gravity fed tub grinder. This size reduction not only achieves the first level of sizing the material but is a further step in the raw material cleaning process and achieves about an 80% reduction in the bulk size of the raw material. This reduction in bulk size increases the ability to transport and store the bio-mass raw material for processing. This is especially critical to plants located in regions that will produce enough bio-mass for year round production of urea (or other products) but the bio-mass being an agricultural byproduct (i.e., a waste stream) is generated cyclically throughout the year (during harvest). Efficient storage in a condensed manner is critical for effective handling and transportation of the input stock and, in addition, reduces storage cost. In a preferred embodiment, an approximate 9,600 pounds per hour may be processed through this step in the system. This step can also be achieved by such means as a hammer mill or other forms of material grinding.

Process Step 6—First in Process Blending/Storage

The next step in the process uses a live bottom blending hopper with an oscillating spreader. This process achieves an increase in the blending of the different types of bio-mass materials to achieve a higher level of material uniformity. This step allows for an increase in raw material quality by achieving homogeneity in the bio-mass mix. The varying types of bio-mass that are brought in to the initial stages of the urea plant are not only non-uniform in size and type of material, but are also non-uniform in process characteristics such as humidity content, BTU (caloric) burn value, density, weight, and mass. The oscillating spreader allows for a better mix of the bio-mass material and the mechanical action of the live bottom blending hopper further achieves the uniformity of size and mix of the bio-mass. This process can also be achieved by shakers and mixers.

Process Step 7—Second in Process Blending/Storage

In the next step the material is transported using an elevating conveyor which gravity feeds the bio-mass into a second live bottom blending hopper with oscillating spreader (see step 6). The same processing done in step 6 is repeated in step 7.

Process Step 8—Blending Augers

Step 8 uses counter rotating screw blending augers to convey and further blend the bio-mass raw material. This step achieves a finer mix of the material and screening of nonorganic material that may still be present. This screening is achieved by a screen mesh located on the bottom of the blending auger. This process can also be achieved by a vibrating screen conveyor or other form of blending and conveyor combination.

Process Step 9—Pellet Mill Feed Storage

The blending auger (step 8) elevates the material to a live bottom blending hopper with oscillating feeder in process step 9. This serves as the pellet mill's feed storage and is a further filtering process for non-organic material, assisting in raw material (bio-mass) size and consistency control. The material is then gravity feed to the next step, the pellet mill—step 10). This process can also be achieved by shakers and mixers.

Process Step 10—Pellet Mill (Pelletizing)

The next step in the process is to pelletize the bio-mass. This may be achieved by using a standard pelletizer. The pellets produced may be in a range of 5/32 to 1/2 inch in size, with pellets in the range of 3/8 to 1/2 inch preferred. In one preferred embodiment, pellet size ranged from 5/32 to 1/4 inch and a pelletized feedstock in the range of 35 pounds per cubic foot to 45 pounds cubic foot was produced. In another preferred embodiment, pellet size ranged from 3/8 to 1/2 inch to produce a pelletized feedstock in the same density range as above. Other densities may be applicable depending on the agricultural bio-mass being blended.

The pelletizing is done to reduce the size of the bio-mass to increase bulk density, reduce the potential fire hazard of bio-mass storage, reduce storage volume, improve material handling, and increase storage longevity (because some bio-mass is seasonal it requires bulk build-up and storage for year-round availability). This process can also be achieved by bracketing or creating range cubes of the bio-mass raw material.

Process Step 11—In Process Pellet Storage

The pelletized bio-mass is then sent to the gasification feed unit (step 12) or to storage (step 11). Either way, the pellets are conveyed using a screened conveyor which has cooling fans located beneath the conveyor to reduce the heat of the pellets (gained from the pelletizing process). This cooling of the pellets prevents the pellets from sweating and building up heat and humidity absorption. This helps maintain bio-mass quality, required for the gasification process. This process can also be achieved by any other means of conveyance that allows for cooling of the material, such as pneumatic conveyors.

Process Step 12—Gasification Feed Unit

To achieve the best possible gasification system, the gasifier must be furnished with a homogenous blend of raw materials (bio-mass) in order to maintain high operations standards. This homogenous blend is primarily accomplished via process steps 6 to 8. In step 12, the gasification feed unit is comprised of a sequential feed, six-chamber, live bottom blender. This achieves fine blending of the bio-mass by distributing pellet physical properties and reduction of day to day raw material variability. This fine blending can also be achieved by any other means of multi-layer mixing.

Process Step 13—Gasifier (Gasification of Bio-Mass)

The gasification of the bio-mass has several sub-level process steps. First the pelletized bio-mass is run through a fine stage crusher and pulverizer. This step is critical in that the pulverizing of the pelletized bio-mass creates a uniform size reduction of bio-mass particles of less than about 1 mm. These uniform micro-particles of finely mixed and blended bio-mass provides the gasifier with material that can be fed in a fine mist that will burn more evenly due to uniformity and size and increased surface area. This improved burn capacity reduces the probability of the production of by-products such as tars, etc. This pulverizing step can also be achieved by means of a hammer mill or any other form of fine grinding. The bio-mass is then fed to the gasifier, which is preferably an up-draft TRME gasifier.

The gasification apparatus has several control facets that help maintain high levels of efficiency and quality control of the product. First, there is an on-demand organic oil injector, which is used to supplement the bio-mass mist in the gasification to maintain a constant, low fluctuating burn of the bio-mass. Computer numeric controls on the gasifier monitor the BTU values of the gasification and adjust accordingly to maintain a uniform burn profile. The computer numeric sensing is what triggers the on-demand organic oil injectors. Secondly, the gasification process also has a feed control system (also computer numerically controlled) that serves as a bio-mass feed regulator that contains a speed adjustment linked to the gasification sensors to maintain the burn temperature at +/−25 degrees C. The speed control speeds up or slows down the bio-mass being fed into the gasifier which serves to regulate the gasification temperature. This process can be achieved by other forms of gasification such as fluidized bed, bubbling fluidized bed, entrained fluidized bed or down-draft gasification units. The quality of the syngas produced addresses technical barrier 4 cited above.

Process Step 14—Recycled Combustibles

Another sub-component of the gasification unit is the recycling of the tars which are produced by the gasification of the bio-mass. The tar is handled by engineering the gas content to obtain a 2-to-1 hydrogen-carbon ratio. A thermal cracking of the tars is achieved, breaking the long carbon chains allowing this process by-product (tar) to be re-introduced into the gasification chamber to produce useful syngas. The products of this whole process are syngas, $CO_2$, and ash. The ash is addressed in step 15 of this process description. The $CO_2$ is addressed in step 16 of this process description.

The gas (syngas) produced by the gasification unit is cooled by running it through a refrigeration loop and the temperature is dropped to less than about 175 degrees C. The gas is run through a multi-staged compression process to increase the gas pressure to about 6,000 to 7,000 psi. This prepares the gas to be fed to the ammonia unit (step 17). This cooling and pressurization is a process requirement because without it, an incomplete ammonia reaction would result. This process can also be achieved by any other means of cooling and pressurization of a gas.

Process Step 15—Ash Disposal

In process step 13, the pelletized feedstock is efficiently gasified in excess of 98% conversion efficiency, leaving only 6 to 9% fly ash based on the weight of the feed material. The ash produced in this process contains no heavy metals and is removed and can be sold as a usable product (fertilizer or for the production of Portland cement).

Process Step 16—$CO_2$ Processing

The $CO_2$ is removed (stripped) from the process (see step 13) and like the syngas, is run through a multi-staged compression process to achieve a pressure of about 6,000 to 7,000 psi. The compressed $CO_2$ is then fed to the urea production unit (see step 18).

Process Step 17—Ammonia Unit (Intermediate Ammonia Production)

This step is known technology and a Haber-Bosch ammonia unit may be used to convert the syngas to ammonia. The ammonia produced in this process is an intermediate product required (contained) for the production of urea and is directly fed to step 18. Other means of processing the syngas to produce ammonia include the use of Fischer-Tropes or any other ammonia producing unit.

Process Step 18—Urea Formation

The production of urea is achieved using a pool-condenser reactor unit which receives both the ammonia produced in step 17 and the $CO_2$ created in the gasification of the bio-mass (see step 16). The urea produced by this unit contains a 46% nitrogen content (by weight). Any other apparatus that converts urea from ammonia may be used at this step of the process.

Process Step 19—Film Dryer or Prilling (Drying of Liquid Urea)

The urea that is produced in step 18 is in liquid form. Though it can be sold in this manner, the storage and ease of transportation is improved by drying the urea. Creating a dried urea is achieved by film drying or prilling. This stabilizes the product. The choice of using a film dryer or priller is purely customer demand based.

Process Step 20—Finish Product Storage

The dried urea is a very stable and relatively inert product. Storage can be handled in many ways and any form of storage that accounts for some form of humidity control is an acceptable means of bulk storage for the product.

II. Modular Arrangement

Referring now to FIGS. 2 to 5, the urea production process may be a modularized process, with process steps 1 to 5 comprising a feedstock preparation module 100, steps 6 to 11 comprising a pelletizing module 200, steps 12 to 15 comprising a gasification module 300, and steps 16 to 19 comprising a urea conversion module 400. The various pieces of process equipment associated with each module have been mapped to the corresponding process steps of FIG. 1.

The feedstock preparation module 100, pelletizing module 200, gasification module 300, and urea conversion module 400 may be arranged for turn-key operation preferably on standard 48-foot flatbed trailers T, respectively. If a smaller size flatbed trailer is used, it may be necessary to divide the individual component parts of the module 100, 200, 300, or 400 into two or more flatbed trailers with appropriate connections being provided.

Each module 100, 200, 300, and 400 is preferably skid-mounted for ease of offloading to a remote site. A portable power plant P may be provided to power one or more of the modules 100, 200, 300, 400. The modules 100, 200, 300, and 400 may be transported to and located and operated in the same geographic location or may be individually located in different geographic locations. Although the process flow and interconnections between various components are not shown in FIGS. 2 to 5, a person of ordinary skill in the art would recognize the flow pattern and the types of connections required for various process components.

Referring now to FIGS. 6 to 9, an alternate preferred embodiment of urea conversion module 400 is shown which may be arranged so as to fit within the footprint of a standard 48-foot flatbed trailer T. Similar to FIGS. 2 to 5 above, the various pieces of equipment associated with the urea conversion module 400 have been mapped to the corresponding process steps of FIG. 1.

While a modular system and method for urea production using a bio-mass feedstock has been described with a certain degree of particularity, many changes may be made in the details of construction and the arrangement of components and steps without departing from the spirit and scope of this disclosure. A system and method according to this disclosure, therefore, is limited only by the scope of the attached claims, including the full range of equivalency to which each element thereof is entitled.

What is claimed is:

1. A method for producing urea from bio-mass, the method comprising:
blending a bio-mass feedstock stream that includes a feedstock component having a different bulk density BTU content than at least one other feedstock component to obtain a substantially homogeneous blend having a consistent bulk density BTU content;
gasifying the homogenous blend in a gasifier; and
combining a resultant $CO_2$ stream from the gasifier with $NH_3$ to form urea.

2. A method according to claim 1 wherein the bio-mass feedstock stream has a moisture content of less than about 15% by weight.

3. A method according to claim 1 wherein the bio-mass feedstock stream includes no more than 1% non-organic matter by weight.

4. A method according to claim 1 further comprising pelletizing the homogenous blend.

5. A method according to claim 4 further comprising the pelletizing step resulting in pellets having substantially the same calorific burn value.

6. A method according to claim 1 further comprising sizing the homogenous blend to a predetermined size.

7. A method according to claim 4 further comprising pulverizing the pellets.

8. A method according to claim 1 further comprising injecting an organic oil into the homogenous blend to maintain a substantially constant temperature of the gasifier within a predetermined range.

9. A method according to claim 1 wherein a temperature of the gasifier when gasifying the pellets does not vary by more than about ±25° C.

10. A method according to claim 1 further comprising the step of cleaning a resultant syngas stream from the gasifier.

11. A method according to claim 1 further comprising the step of compressing a resultant syngas stream from the gasifier to a high pressure of about 6,000 to 7,000 psi.

12. A method according to claim 1 further comprising the step of processing $NH_3$ in a bypass recycling loop at a 30% conversion rate at a high pressure of about 6,000 to 7,000 psi.

13. A method according to claim 1 wherein the blending occurs at a geographical location different from where the gasification occurs.

14. A method according to claim 1 wherein all equipment associated with at least one of the blending and gasification is contained within a footprint of a standard flatbed truck trailer.

15. A method according to claim 1 wherein all equipment associated with at least one of the blending and gasification is skid mounted.

* * * * *